(12) United States Patent
Nadal

(10) Patent No.: US 6,221,064 B1
(45) Date of Patent: Apr. 24, 2001

(54) TUBE COUPLING DEVICE FOR CONNECTING A TUBULAR RIGID STEM TO A FLEXIBLE CATHETER TUBE

(75) Inventor: Guy Nadal, Poitiers (FR)

(73) Assignee: B. Braun Celsa, Boulogne-Billancourt (FR)

( * ) Notice: Subject to any disclaimer, the term of this patent is extended or adjusted under 35 U.S.C. 154(b) by 0 days.

(21) Appl. No.: 09/359,674

(22) Filed: Jul. 23, 1999

(30) Foreign Application Priority Data

Jul. 27, 1998 (FR) .................................................. 98 09560

(51) Int. Cl.$^7$ .................................................. A61M 25/16
(52) U.S. Cl. ............................................. 604/533; 604/905
(58) Field of Search ..................................... 604/533–538, 604/285, 264, 905; 285/248, 259

(56) References Cited

U.S. PATENT DOCUMENTS

| | | |
|---|---|---|
| 4,880,414 | * 11/1989 | Whipple . |
| 4,963,133 | * 10/1990 | Whipple . |
| 5,026,344 | * 6/1991 | Dijkstra et al. . |
| 5,417,656 | * 5/1995 | Ensminger et al. . |
| 5,423,776 | * 6/1995 | Haindl . |
| 5,620,427 | * 4/1997 | Werschmidt et al. ................ 604/283 |
| 5,637,102 | * 6/1997 | Tolkoff et al. ....................... 604/283 |

FOREIGN PATENT DOCUMENTS

2703593 * 10/1994 (FR) .
2750055 * 12/1997 (FR) .

* cited by examiner

Primary Examiner—Wynn Wood Coggins
Assistant Examiner—Manuel Mendez
(74) Attorney, Agent, or Firm—Rothwell, Figg, Ernst & Manbeck

(57) ABSTRACT

The invention relates to a tube coupling device for connecting a tubular rigid stem to a flexible catheter tube which is adapted to be arranged around said tubular rigid stem, the flexible catheter tube having a proximal free end, the tube coupling device having a main axis, a wall, at least an inner lumen extending along said main axis, through the wall, and two opposite radially non-deformable distal and proximal free ends, said inner lumen axially widening out towards the proximal free end of the tube coupling device, so that the proximal free end of the flexible catheter tube radially expands in the widening when arranged around the tubular rigid stem, said widening being delimited, along the main axis, at a first end, by the proximal free end of the tube coupling device, and, at a second opposite end by an internal annular flange extending from the wall of the tube coupling device, at a location along the main axis which is intermediate between the proximal and the distal free ends of the tube coupling device, wherein the flange comprises slots, so that said flange is divided into different sectors.

8 Claims, 5 Drawing Sheets

FIG_1

Figure 1:
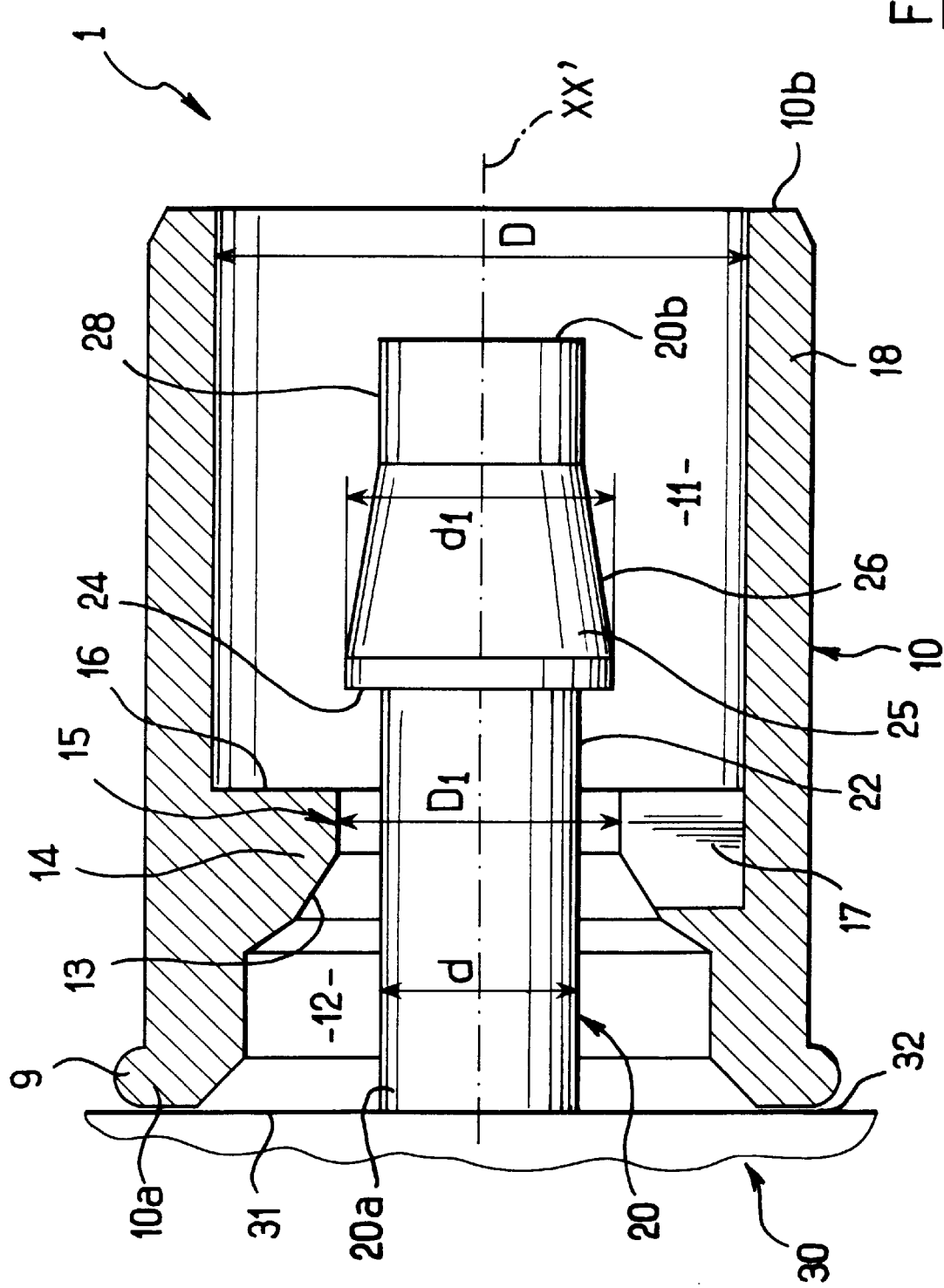

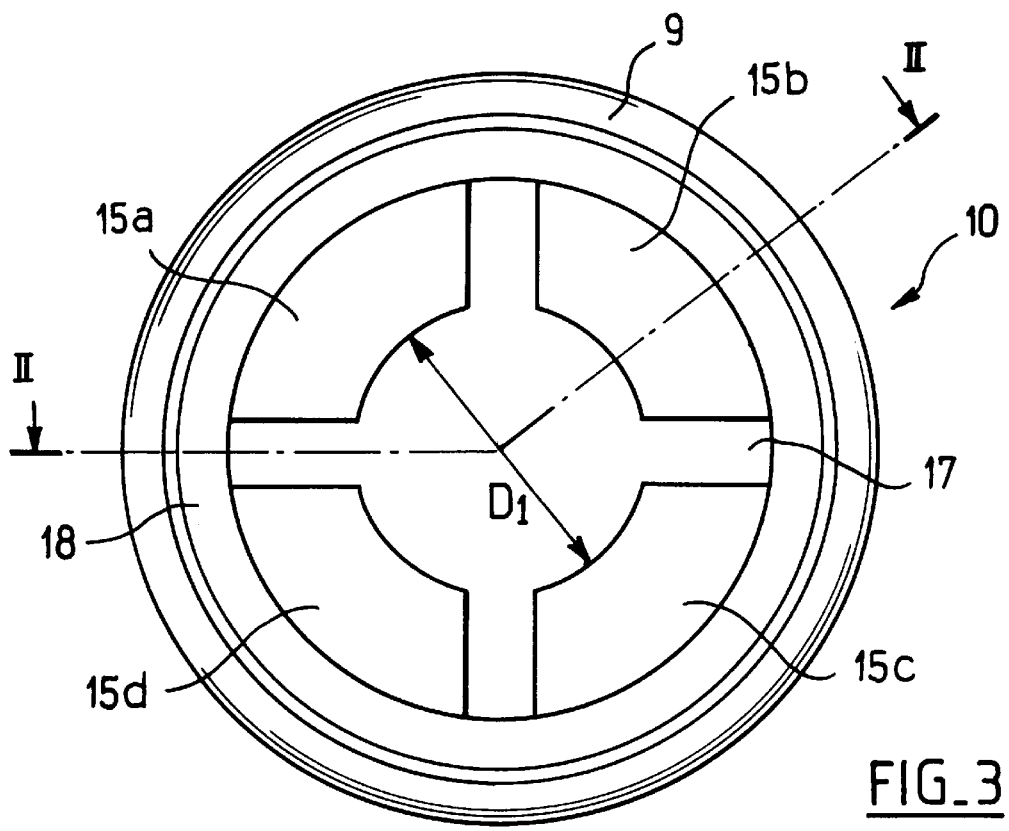
FIG_3
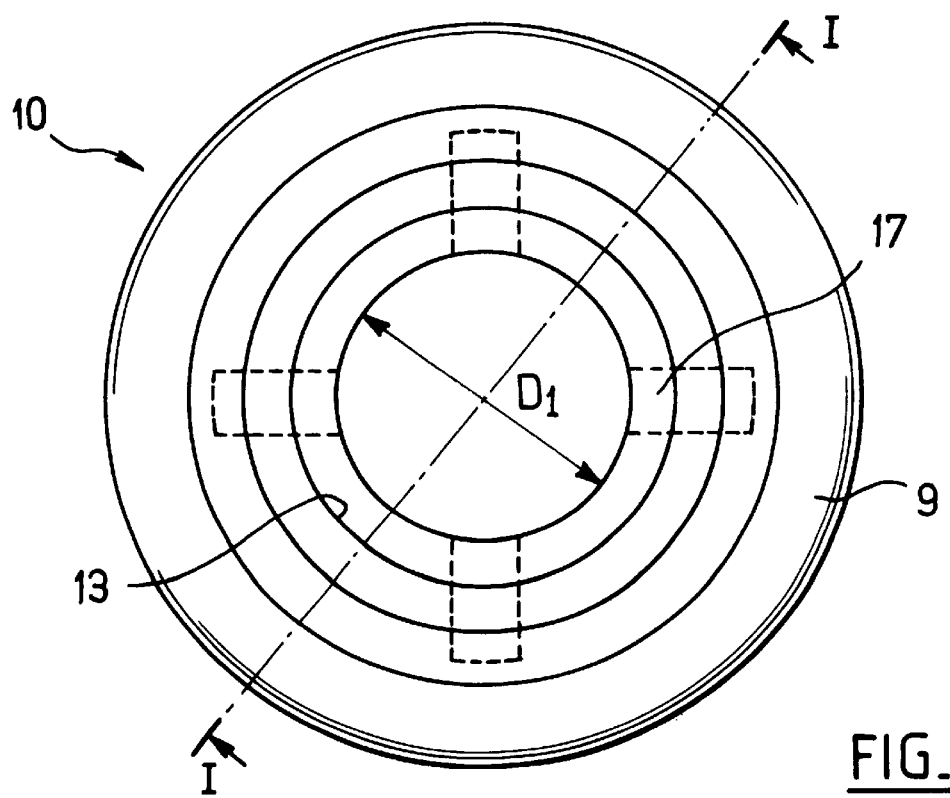
FIG_4

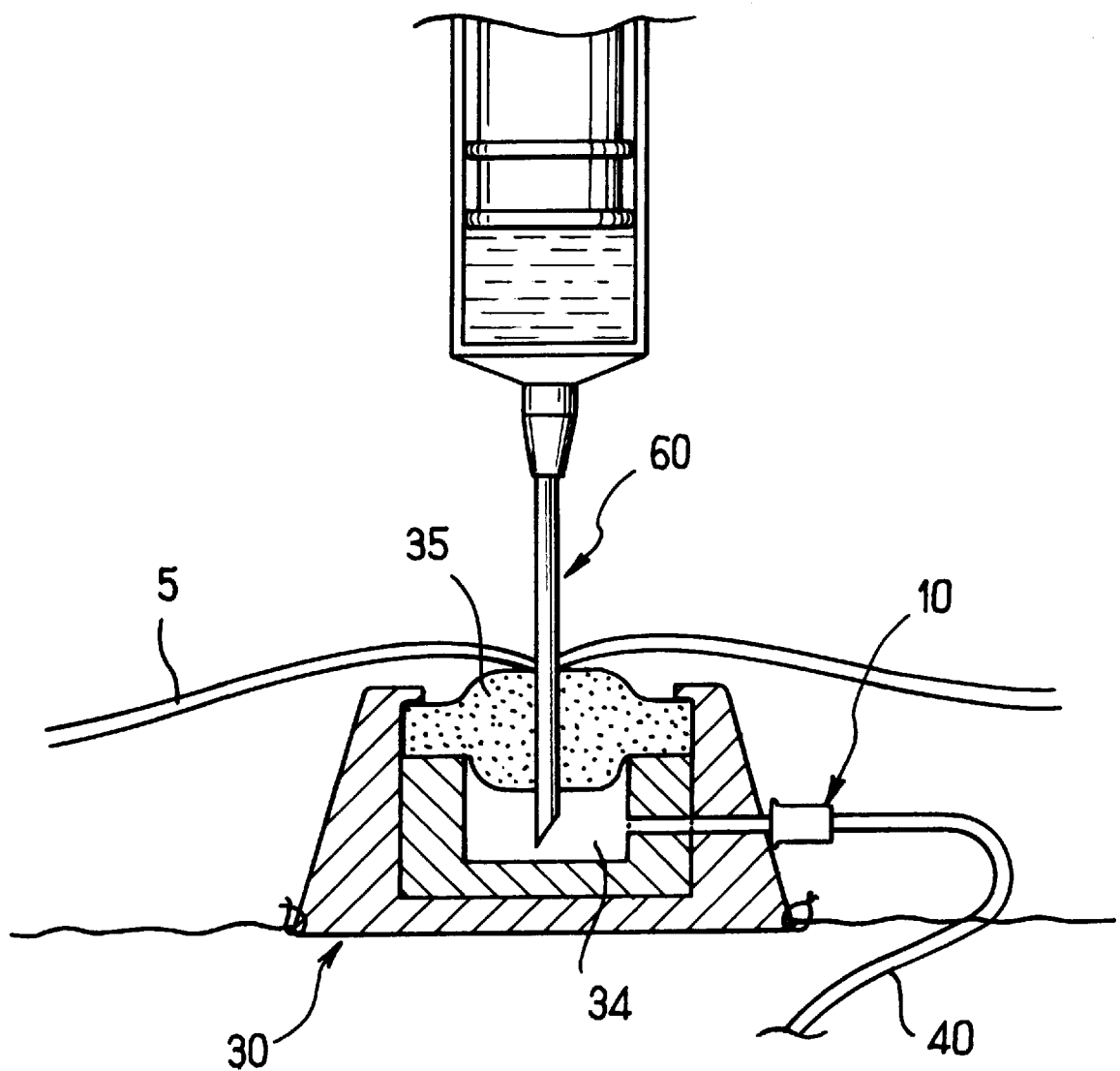
FIG_6

TUBE COUPLING DEVICE FOR CONNECTING A TUBULAR RIGID STEM TO A FLEXIBLE CATHETER TUBE

BACKGROUND OF THE INVENTION

1. The Field of the Invention

The invention relates to a medical tube coupling system between a tubular rigid stem and a flexible catheter tube.

Nowadays, different coupling systems of that type are known, for example for connecting an injection needle and a medical catheter.

A privileged application of the invention is relative to the connection between elements adapted to be entirely implanted within a human body, under the skin.

2. Background Art

U.S. Pat. No. 5,417,656, FR-A-2 703 793 and FR-A-2 750 055 disclose different embodiments for coupling a flexible catheter tube to the rigid stem of a port catheter system adapted to be subcutaneously implanted in a human body.

Drawbacks remain in the prior art embodiments.

Some of the prior art systems are not easy to manipulate by the practitioner. These systems often comprise too many elements which have to slide one relative to the other. Their respective clearance and imperviousness are sometimes not appropriate or induce too high costs.

SUMMARY OF THE INVENTION

To improve the reliability, the effectiveness and the costs of the prior art embodiments, the invention suggests an improved tube coupling device for connecting a tubular rigid stem to a flexible catheter tube which is adapted to be arranged around said tubular rigid stem, the flexible catheter tube having a proximal free end, the tube coupling device having a main axis, a wall, at least an inner lumen extending along said main axis, through the wall, and two opposite radially non-deformable distal and proximal free ends, said inner lumen axially widening out towards the proximal free end of the tube coupling device, so that the proximal free end of the flexible catheter tube radially expands in the widening when arranged around the tubular rigid stem, said widening being delimited, along the main axis, at a first end, by the proximal free end of the tube coupling device, and, at a second opposite end by an internal annular flange extending from the wall of the tube coupling device, at a location along the main axis which is intermediate between the proximal and the distal free ends of the tube coupling device, wherein the flange comprises slots, so that said flange is divided into different sectors.

It is another object of the invention to improve the engagement of the tube coupling around the flexible catheter tube previously arranged around the tubular rigid stem.

So, the invention suggests that the inner annular flange of the tube coupling device axially ends, within the inner lumen:

at a first end opposite to the widening of the inner lumen, in a shoulder substantially perpendicular to the main axis, so that the lumen has, there, a sharp increasing of diameter, and at a second end, adjacent the widening, in a chamfered edge.

Yet another object of the present invention is to improve the guiding of the tube coupling device around the catheter tube.

Thus, according to another preferred feature of the invention, beyond the inner annular flange of the coupling device and towards the distal end thereof, the lumen of the tube coupling device preferably extends within an axial cylindrical skirt dimensioned for receiving therein a ring, said ring being adapted to be arranged around the flexible catheter tube.

Still another object of the invention is to provide a medical coupling assembly reducing the number of elements for coupling a stem to a catheter tube, while improving the reliability and imperviousness of the coupling.

Accordingly, the typical medical coupling assembly of the invention preferably comprises:

a tubular rigid stem, said stem having an annular outer excrescence located towards a first free end thereof, a flexible catheter tube having a proximal free end, said flexible catheter tube being adapted to be arranged around the stem, and a tube coupling device adapted to be arranged around the flexible catheter tube for connecting the flexible catheter tube to the tubular rigid stem, the tube coupling device having a main axis, a wall, at least an inner lumen extending along said main axis, through the wall, and two opposite distal and proximal free ends, said inner lumen widening out towards the proximal free end of the tube coupling device, the widening being delimited, along the main axis, at a first end by the proximal free end of the tube coupling device, and, at a second opposite end, by an internal annular flange extending from the wall of the tube coupling device, so that when the flexible catheter tube is arranged around the tubular rigid stem, beyond the annular outer excrescence, and when the tube coupling device is arranged around the flexible catheter tube, the flexible catheter tube expands radially at its proximal free end within the widening of the tube coupling device, wherein the inner annular flange of the tube coupling device is provided with slots, so that when the catheter tube is arranged around the stem and when the tube coupling is arranged around the catheter tube, a portion of the flexible catheter tube is jammed into these slots.

Preferably, the above-mentioned assembly further comprises, according to the invention, a stop means adjacent the tubular rigid stem, and the flexible catheter tube and the tube coupling are respectively arranged substantially in contact with said stop means, in an engaged position, so that the inner annular flange of the tube coupling device and the annular outer excrescence of the tubular rigid stem are axially set off, and the inner annular flange is axially located closer to the stop means than the annular outer excrescence.

Preferably, according to another feature of the invention:

the annular outer excrescence of the rigid stem of the medical assembly has a first shoulder which sharply reduces the external diameter of the stem, the inner annular flange of the tube coupling axially ends in a second shoulder sharply enlarging the diameter of the inner lumen of the tube coupling device, and when the flexible catheter tube is arranged around the tubular rigid stem and when the tube coupling device is arranged around the flexible catheter tube, the first shoulder of the excrescence is axially facing the second shoulder of the inner annular flange, the first and second shoulders having substantially equal diameters.

The substantially equal diameters of the first and second shoulders improve the coupling between a catheter tube and the stem, while limiting a possible non-authorized withdrawal of the catheter tube.

Finally, it is another object of the invention to provide an improved coupling between a port catheter system and a catheter tube adapted to be subcutaneously implanted in a blood vessel.

Figure 2:
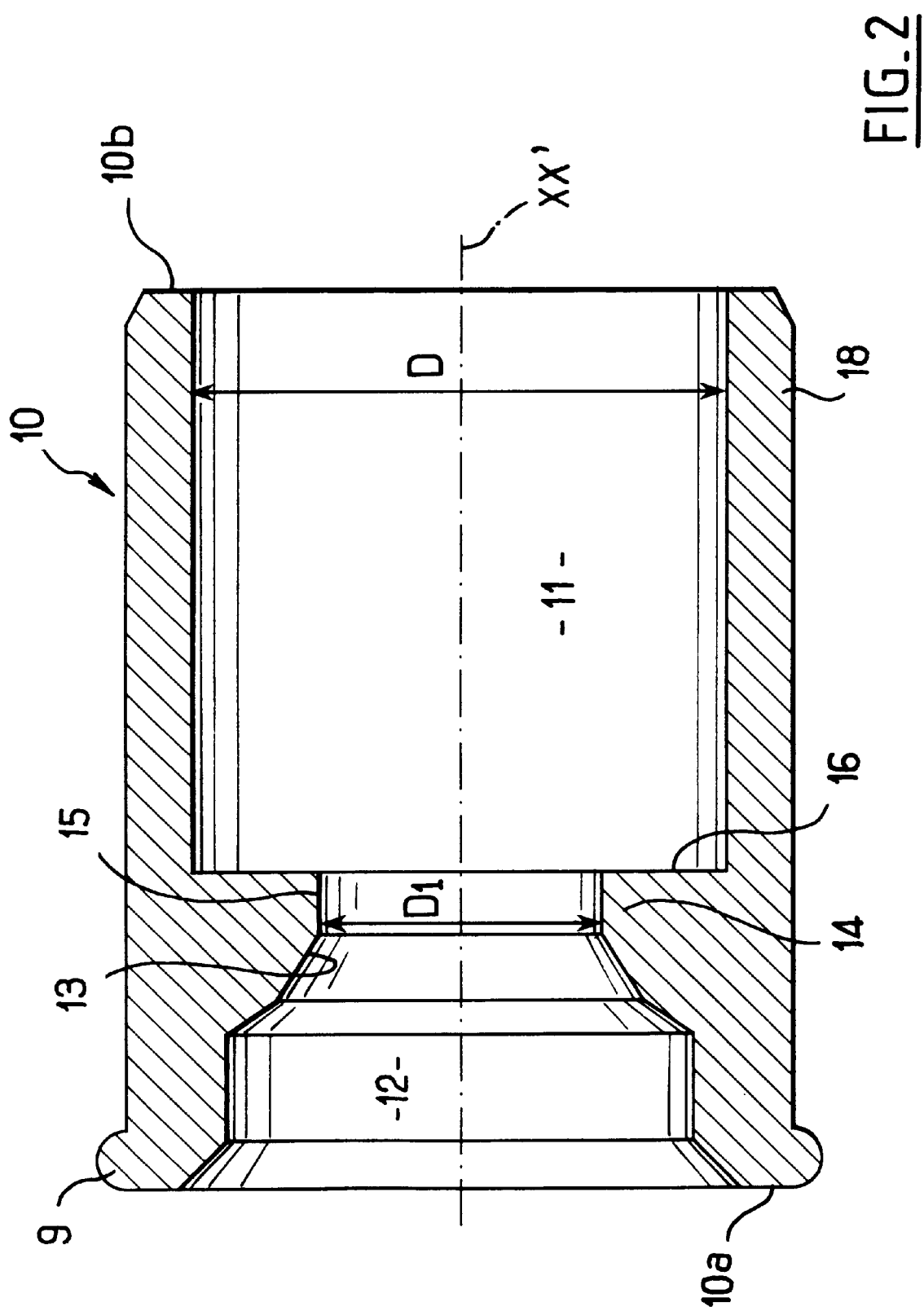
Figure 5:
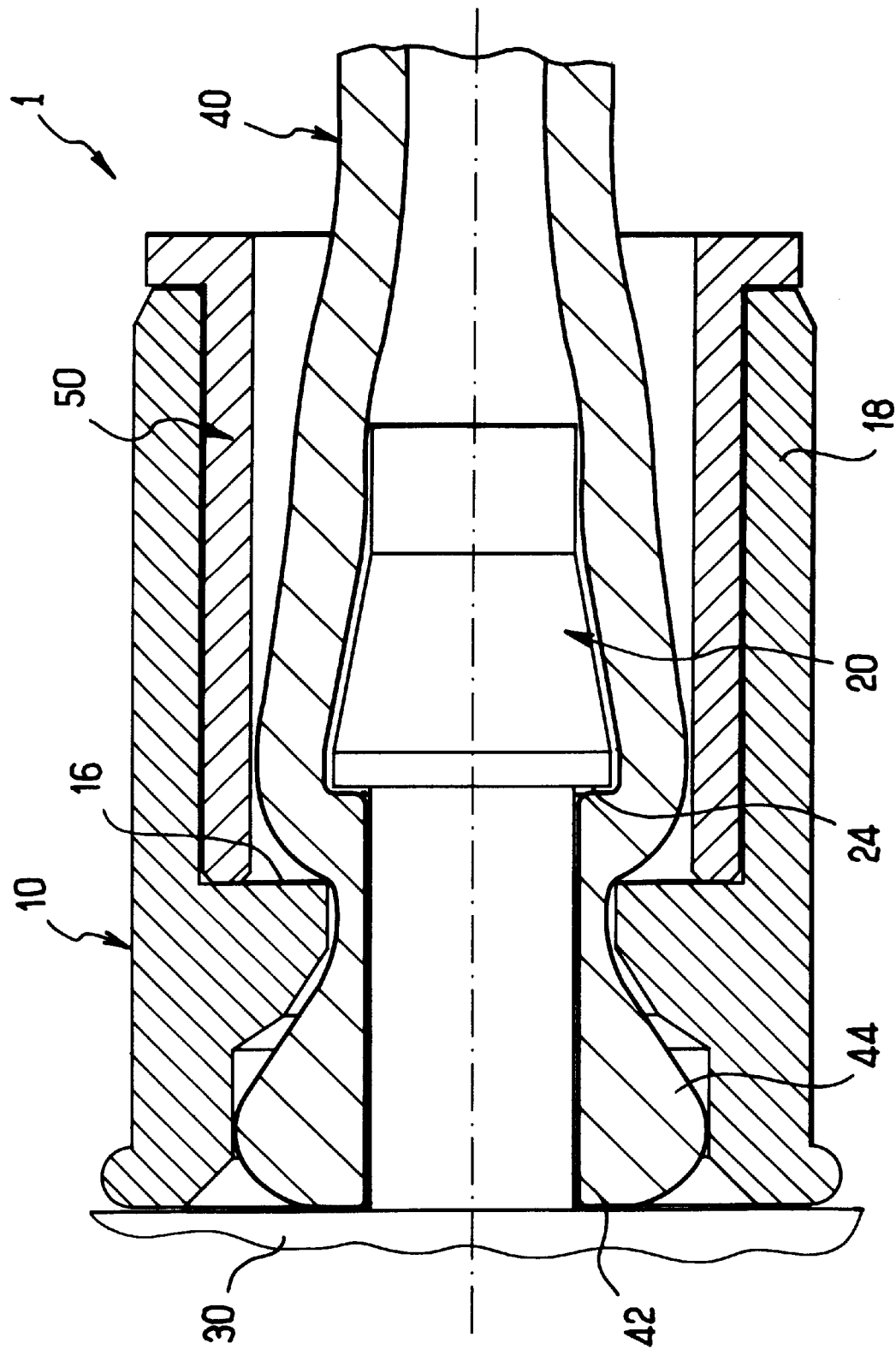

The invention and its implementation will become even clearer with the aid of the following description given with reference to the drawings, in which:

FIG. 1 is a sectioned view, taken on the line II—II, of the ring mounted on the stem, without the flexible catheter tube, FIG. 2 is a sectioned view, taken in another section plane I—I, of the ring alone, FIG. 3 is a view from above, of the ring shown in FIG. 2, FIG. 4 is a view from below, of the ring shown in FIG. 2, FIG. 5 is a view of the whole unit assembled, FIG. 6 is a sectioned view of the unit implanted under a patient's skin.

In FIG. 1 (showing a section taken on the line II—II of FIG. 3), a tubular ring 10 extending along a main axis xx' and having a proximal (non-slitted) radially non-deformable free end 10a and a distal radially non-deformable free end 10b along this axis can be seen, shown in its state before use. This ring also has an internal duct 11 for housing a tubular rigid rod 20 (or stem) forming the connector of a vascular access system 30 (also called an implantable chamber) which is generally arranged subcutaneously beneath a patient's skin (see FIG. 6) in order to administer (injection) a fluid treating product (a drip) to the patient or to withdraw a body fluid such as blood from the patient, by means of a flexible tube 40 (a catheter) connected to the said system 30 (see FIGS. 5 and 6). In this embodiment, the implantable chamber 30 and the rigid stem 20 are formed integrally, for example by moulding, of biocompatible plastic material or of metal. The ring 10 is also made of biocompatible plastic material.

The ring 10 has, at its proximal free end 10a, (that is, its end adjacent the implantable chamber in the implanted condition of the unit) a widening out (or flared) portion 12 inside which, as shown in FIG. 5, the flexible tube 40 can expand radially (radial swelling) for reasons which will be explained in greater detail below, when it is fitted around the stem 20.

This widening out portion 12 is delimited internally, in the direction of the distal end 10b of the ring 10, by a substantially indeformable, rigid block 14 defining an annular flange (or projection) 15 (see also FIG. 2 showing the ring 10 viewed in the section plane I—I of FIG. 4). This block 14 is in the form of an inclined surface 13 or ramp oriented such that the diameter D of the internal duct 11 of the ring 10 decreases gradually towards its distal end 10b. The flange 15 terminates, on the side facing the distal end 10b of the ring 10, in a shoulder 16 substantially perpendicular to the axis xx', thus abruptly increasing the diameter D of the internal duct 11 of the ring 10 in this location. This annular flange 15 is divided into sectors 15a, 15b, 15c, 15d, as can be seen in FIGS. 2 to 4, every two sectors being separated by a slot 17.

Finally, the annular projection 15 is extended, towards the distal end 10b of the ring 10, by an annular skirt 18 (or barrel) inside which an annular sleeve (a ring) 50 can be placed (see FIG. 5) for centering the tube 40 on the stem 20, as will also be explained below.

The ring 10 typically measures between approximately 7 and 9 millimeters and preferably 8 millimeters between its ends. It also has an external annular protuberance 9 for serving as an abutment for a positioning implement such as a pair of forceps.

The stem 20, of outside diameter d, has a particular shape such that the flexible catheter 40 can be mounted around it (see FIG. 5) in a fluid-tight manner in relation to the fluid flowing through the said catheter 40. Starting from the outer surface 31 of the implantable chamber 30, the stem 20 has, first of all, a straight, cylindrical portion 22 extending along the axis xx'. This portion 22 has a circular cross-section and typically measures a few millimeters in length.

The stem 20 then has an annular enlarged portion 25 (i.e. an excrescence) defined by a rear shoulder 24, abruptly increasing the diameter d of the rod, followed by an inclined conical portion 26 the diameter of which decreases so as to be substantially equal to that of the straight portion towards the free front end 20b of the stem 20.

Finally, the conical portion 26 is extended, again towards the free end 20b of the stem 20, by a second straight portion 28 arranged as an extension of the first cylindrical portion 22.

The stem 20 thus measures about 7 millimeters between the surface 31 of the implantable chamber 30 and the free end 20b.

The diameter D1 of the shoulder 16 of the projection 15 and the diameter d1 of the shoulder 24 of the excrescence 25 are comparable and the difference between D1 and d1 should not exceed the thickness of the flexible catheter tube 40.

The use of the tube coupling device 1 thus described for positioning a flexible catheter 40 on an implantable chamber 30 is very easy and is illustrated, in particular, by FIG. 5.

The flexible and hollow catheter 40 is force-fitted, starting from its proximal end 42, around the stem 20 on the straight portion 28 thereof. The catheter 40 is passed over the conical portion 28 of the stem 20 so as to be resiliently deformed slightly, expanding radially to fit this shape. Finally, its end 42 is passed over the shoulder 24 of the excrescence 25 of the stem 20 and is brought into contact with the surface 31 of the implantable chamber 30. In this position, the tube 40 clings to the stem 20 but can easily be withdrawn by pulling thereon.

The ring 10 is then passed around the catheter 40 by action on the external annular protuberance 9 by means of a pair of forceps and is slid, around the catheter, along the rod until its proximal end 10a is in contact with the surface 31 of the implantable chamber 30 which thus serves as an abutment 32 (or a stop means) for the stem 20. For this purpose, the internal flange 15 of the ring 10 is passed over the projecting enlarged portion 25 of the stem 20 already covered by the catheter 40, and is brought beyond the enlarged portion 25 so that the enlarged portion 25 and the projection 15 are offset axially, the projection then being disposed closer to the surface 31 (and thus to the abutment 32) than the enlarged portion. The result of this operation is to displace a portion of the flexible plastic material constituting the catheter 40 towards the surface 31 of the implantable chamber. The catheter thus expands radially (local deformation) and becomes lodged in the flared portion 12 provided for this purpose in the ring 10, forming a teardrop shape 44 when viewed in section.

In this position, the catheter 40 is fixed to the stem 20 firmly and in a fluid-tight manner in relation to the fluid transported thereby. The catheter is immobilized with respect to axial translation by the cooperation of the shoulders 16 and 24 of the ring 10 and of the stem 20 which face one another a few tenths of a millimeter apart.

Moreover, since the catheter 40 is made of flexible, plastic material (rubber, silicone) it can pass into and be wedged in the slots 17 of the ring 10, further improving its connection to the stem 20.

An annular sleeve 50 can then be positioned around the catheter 40 in the space 19 inside the skirt 18 of the ring 10 at the level of its distal end 10b.

It then remains to implant the unit 1 thus formed subcutaneously, as shown in FIG. 6, in which the implantable chamber 30 can be seen implanted at a shallow depth beneath a patient's skin 5. A needle suitable for any appropriate injection and/or puncture system is shown at 60. To close the top of its internal space 34 with the ability to form a product reservoir, the implantable chamber 30 comprises an upper wall 35 which can be perforated by the needle 60 whilst being self-sealing and being formed, for example, as a block of silicone-coated plastics material.

What is claimed is:

1. A tube coupling device for connecting a tubular rigid stem to a flexible catheter tube which is adapted to be arranged around said tubular rigid stem, the flexible catheter tube having a proximal free end, the tube coupling device having a main axis, a wall, at least one inner lumen extending along said main axis, through the wall, and two opposite radially non-deformable distal and proximal free ends, said inner lumen axially widening out towards the proximal free end of the tube coupling device, so that the proximal free end of the flexible catheter tube radially expands in the widening when arranged around the tubular rigid stem, said widening being delimited, along the main axis, at a first end, by the proximal free end of the tube coupling device, and, at a second opposite end by an internal annular flange protruding from the wall of the tube coupling device, in said at least one inner lumen, at a location along the main axis which is intermediate between the proximal and the distal free ends of the tube coupling device, wherein the flange comprises slots, so that said flange is divided into different sectors.

2. The tube coupling device of claim 1, wherein the inner annular flange axially ends, within said inner lumen:

at a first end opposite to the widening of the inner lumen, in a shoulder substantially perpendicular to the main axis, so that the lumen has, there, a sharp increasing of diameter, and at a second end, adjacent the widening, in a chamfered edge.

3. The tube coupling device of claim 1, wherein, beyond the inner annular flange and towards the distal end of the tube coupling device, the lumen extends within an axial cylindrical skirt dimensioned for receiving therein a tubular ring adapted to be arranged around the flexible catheter tube.

4. A medical coupling assembly, comprising:

a tubular rigid stem, said stem having an annular outer excrescence located towards a first free end thereof, a catheter tube having a proximal free end, said flexible catheter tube being adapted to be arranged around the stem, and being made of a deformable material, and a tube coupling device adapted to be arranged around the catheter tube for connecting the catheter tube to the tubular rigid stem, the tube coupling device having a main axis, a wall, at least one inner lumen extending along said main axis, through the wall, and two opposite distal and proximal free ends, said inner lumen widening out towards the proximal free end of the tube coupling device, the widening being delimited, along the main axis, at a first end by the proximal free end of the tube coupling device, and, at a second opposite end, by an inner annular flange protruding from the wall of the tube coupling device, in said at least one inner lumen at a location along the main axis which is intermediate between the proximal and the distal free ends of the tube coupling device, so that when the catheter tube is arranged around the tubular rigid stem, beyond the annular outer excrescence, and when the tube coupling device is arranged around the catheter tube, the catheter tube expands radially at its proximal free end within the widening of the tube coupling device, wherein the inner annular flange of the tube coupling device is provided with slots, and the material of the catheter tube is deformable in such a way that when the catheter tube is arranged around the stem and when the tube coupling is arranged around the catheter tube, a portion of the catheter tube is jammed and wedged into said slots.

5. The assembly of claim 4, wherein a stop means is provided adjacent the tubular rigid stem, and when the catheter tube and the tube coupling are respectively arranged substantially in contact with said stop means, in an engaged position:

the inner annular flange of the tube coupling device and the annular outer excrescence of the tubular rigid stem are axially set off, and the inner annular flange is axially located closer to the stop means than the annular outer excrescence.

6. The assembly of claim 5 wherein:

the stem is a rigid tube extending from a port opening of a port catheter system adapted to be subcutaneously implanted, the stop means of the tubular rigid stem is defined by an external surface of a housing of said port catheter system containing the port opening, and the catheter tube is a catheter adapted to be implanted in a blood vessel.

7. The medical assembly according to claim 4, wherein:

the annular outer excrescence of the rigid stem has a first shoulder which sharply reduces the external diameter of the stem, the inner annular flange of the tube coupling axially ends in a second shoulder sharply enlarging the diameter of the inner lumen of the tube coupling device, and when the catheter tube is arranged around the tubular rigid stem and when the tube coupling device is arranged around the catheter tube, the first shoulder of the excrescence is axially facing the second shoulder of the inner annular flange, the first and second shoulders having substantially equal diameters.

8. A medical coupling assembly, comprising:

a tubular rigid stem, said stem having an annular outer excrescence located towards a first free end thereof, a catheter tube having a proximal free end, said catheter tube being adapted to be arranged around the stem and being made of a deformable material, a tube coupling device adapted to be arranged around the catheter tube for connecting the catheter tube to the tubular rigid stem, the tube coupling device having:

a main axis, a wall, at least one inner lumen extending along said main axis, through the wall, two opposite distal and proximal free ends, said at least one inner lumen widening out towards the proximal free end of the tube coupling device, the widening being delimited, along the main axis, at a first end by the proximal free end of the tube coupling device, and, at a second opposite end, by an inner annular flange extending from the wall of the tube coupling device in said at least one inner lumen, at a location along the main axis which is intermediate between the proximal and the distal free ends of the tube coupling device, so that when the catheter tube is arranged around the tubular rigid stem, beyond the annular outer excrescence, and when the tube coupling device is arranged around the catheter tube, the catheter tube expands radially at its proximal free end within the widening of the tube coupling device, an axial cylindrical skirt within which the lumen of the tube coupling device extends beyond the inner annular flange and at the distal end of the tube coupling device, wherein the inner annular flange of the tube coupling device being provided with slots, and the catheter tube is deformable in such a way that when the catheter tube is arranged around the stem and when the tube coupling is arranged around the catheter tube, a portion of the flexible catheter tube is jammed into said slots, and wherein the medical coupling assembly further comprises a tubular ring which is arranged around the catheter tube and inside the axial cylindrical skirt when said catheter tube is arranged around the stem and when the tube coupling device is arranged around the catheter tube.

* * * * *